United States Patent [19]

Becker et al.

[11] Patent Number: 5,594,101
[45] Date of Patent: Jan. 14, 1997

[54] ANTI-OBESITY PROTEINS

[75] Inventors: Gerald W. Becker; John E. Hale, both of Fishers; Warren C. MacKellar, Plainfield, all of Ind.

[73] Assignee: Eli Lilly and Company, Indianapolis, Ind.

[21] Appl. No.: 398,021

[22] Filed: Mar. 3, 1995

[51] Int. Cl.$^6$ .............................. A61K 38/00; C07K 5/12; C07K 14/00
[52] U.S. Cl. ........................... 530/317; 530/324; 530/350
[58] Field of Search ................................... 530/350, 324, 530/317; 514/11, 12

[56] References Cited

U.S. PATENT DOCUMENTS 4,626,549  12/1986  Molloy et al. ........................... 514/651

FOREIGN PATENT DOCUMENTS

WO96/05309  2/1996  WIPO.

OTHER PUBLICATIONS

Methods in Enzymology, vol. 68, issued 1979, Brown et al, "Chemical Synthesis and Cloning of Tyrosine trn Gene", pp. 109–151.
Document No. 08/381,048 Name DiMarchi, et al. Filing Date Jan. 31, 1995.
Document No. 08/383,638 Name Basinski, et al. Filing Date Feb. 6, 1995.
Document No. 08/381,033 Name DiMarchi, et al. Filing Date Jan. 31, 1995.
Document No. 08/383,631 Name Basinski, et al. Filing Date Feb. 6, 1995.
Document No. 08/381,265 Name DiMarchi, et al. Filing Date Jan. 31, 1995.
Document No. 08/383,648 Name Basinski, et al. Filing Date Feb. 6, 1995.
Document No. 08/381,247 Name DiMarchi, et al. Filing Date Jan. 31, 1995.
Document No. 08/383/632 Name Basinski, et al. Filing Date Feb. 6, 1995.
Document No. 08/381,266 Name DiMarchi, et al. Filing Date Jan. 31, 1995.
Document No. 08/384,492 Name DiMarchi, et al. Filing Date Feb. 6, 1995.
Document No. 08/381,047 Name DiMarchi, et al. Filing Date Jan. 31, 1995.
Document No. 08/383,649 Name Basinski, et al. Filing Date Feb. 6, 1995.
Document No. 08/381,057 Name DiMarchi, et al. Filing Date Jan. 31, 1995.
Document No. 08/381,050 Name DiMarchi, et al. Filing Date Jan. 31, 1995.
Document No. 08/381,034 Name DiMarchi, et al. Filing Date Jan. 31, 1995.
Document No. 08/381,040 Name DiMarchi, et al. Filing Date Jan. 31, 1995.
Document No. 08/381,163 Name DiMarchi, et al. Filing Date Jan. 31, 1995.
Document No. 08/381,054 Name DiMarchi, et al. Filing Date Jan. 31, 1995.
Document No. 08/381,041 Name DiMarchi, et al. Filing Date Jan. 31, 1995.
Document No. 08/381,370 Name DiMarchi, et al. Filing Date Jan. 31, 1995.
Document No. 08/381,451 Name DiMarchi, et al. Filing Date Jan. 31, 1995.
Document No. 08/383,658 Name Basinski, et al. Filing Date Feb. 6, 1995.
Document No. 08/381,031 Name DiMarchi, et al. Filing Date Jan. 31, 1995.
Document No. 08/383,639 Name Basinski, et al. Filing Date Feb. 6, 1995.
Document No. 08/381,458 Name DiMarchi, et al. Filing Date Jan. 31, 1995.
Document No. 08/384,183 Name Basinski, et al. Filing Date Feb. 6, 1995.
Document No. 08/381,661 Name DiMarchi, et al. Filing Date Jan. 31, 1995.
Document No. 08/384,292 Name Basinski, et al. Filing Date Feb. 6, 1995.
Document No. 08/381,666 Name DiMarchi, et al. Filing Date Jan. 31, 1995.
Document No. 08/406,354 Name DiMarchi, et al. Filing Date Mar. 17, 1995.
Document No. 08/398,021 Name Becker, et al. Filing Date Mar. 3, 1995.
Document No. 08/381,049 Name DiMarchi, et al. Filing Date Jan. 31, 1995.
Document No. 08/381,037 Name DiMarchi, et al. Filing Date Jan. 31, 1995.
Document No. 08/384,493 Name Basinski, et al. Filing Date Feb. 6, 1995.
Document No. 08/381,264 Name Heath, et al. Filing Date Jan. 31, 1995.
Chem. Abstract 94–304407/38, Nagata Sangyo Co. Ltd. (Mar. 29, 1993).
Zhang, et al., "Positional cloning of the mouse obese gene and its human homologue", *Nature*, 372:1, 425–432 (Dec. 1, 1994).
Rink, "In search of a satiety factor", *Nature*, 372:1, 406–407 (Dec. 1, 1994).
Flam, "Obesity Gene Discovery May Help Solve Weighty Problem", *Science*, 266, 1477–1478 (Dec. 2, 1994).

*Primary Examiner*—Elizabeth C. Weimar
*Assistant Examiner*—S. G. Marshall
*Attorney, Agent, or Firm*—Steven P. Caltrider; David E. Boone

[57] ABSTRACT

The present invention provides anti-obesity proteins, which when administered to a patient regulate fat tissue. Accordingly, such agents allow patients to overcome their obesity handicap and live normal lives with much reduced risk for type II diabetes, cardiovascular disease and cancer.

6 Claims, No Drawings

ANTI-OBESITY PROTEINS

FIELD OF THE INVENTION

The present invention is in the field of human medicine, particularly in the treatment of obesity and disorders associated with obesity. Most specifically, the invention relates to anti-obesity proteins that, when administered to a patient, regulate fat tissue.

BACKGROUND OF THE INVENTION

Obesity, and especially upper body obesity, is a common and very serious public health problem in the United States and throughout the world. According to recent statistics, more than 25% of the United States population and 27% of the Canadian population are over weight. Kuczmarski, *Amer. J. of Clin. Nut.* 55: 495S–502S (1992); Reeder et. al., *Can. Med,. Ass. J.*, 23:226–233 (1992). Upper body obesity is the strongest risk factor known for type II diabetes mellitus, and is a strong risk factor for cardiovascular disease and cancer as well. Recent estimates for the medical cost of obesity are $150,000,000,000 world wide. The problem has become serious enough that the surgeon general has begun an initiative to combat the ever increasing adiposity rampant in American society.

Much of this obesity induced pathology can be attributed to the strong association with dyslipidemia, hypertension, and insulin resistance. Many studies have demonstrated that reduction in obesity by diet and exercise reduces these risk factors dramatically. Unfortunately these treatments are largely unsuccessful with a failure rate reaching 95%. This failure may be due to the fact that the condition is strongly associated with genetically inherited factors that contribute to increased appetite, preference for highly caloric foods, reduced physical activity, and increased lipogenic metabolism. This indicates that people inheriting these genetic traits are prone to becoming obese regardless of their efforts to combat the condition. Therefore, a new pharmacological agent that can correct this adiposity handicap and allow the physician to successfully treat obese patients in spite of their genetic inheritance is needed.

The ob/ob mouse is a model of obesity and diabetes that is known to carry an autosomal recessive trait linked to a mutation in the sixth chromosome. Recently, Yiying Zhang and co-workers published the positional cloning of the mouse gene linked with this condition. Yiying Zhang et al. *Nature* 372: 425–32 (1994). This report disclosed a gene coding for a 167 amino acid protein with a 21 amino acid signal peptide that is exclusively expressed in adipose tissue. The report continues to disclose that a mutation resulting in the conversion of a codon for arginine at position 105 to a stop codon results in the expression of a truncated protein, which presumably is inactive.

Physiologists have postulated for years that, when a mammal overeats, the resulting excess fat signals to the brain that the body is obese which, in turn, causes the body to eat less and burn more fuel. G. R. Hervey, *Nature* 227: 629–631 (1969). This "feedback" model is supported by parabiotic experiments that implicate a circulating hormone controlling adiposity. Based on this model, the protein, which is apparently encoded by the ob gene, is now speculated to be an adiposity regulating hormone.

Pharmacological agents that are biologically active and mimic the activity of this protein are useful to help patients regulate their appetite and metabolism and thereby control their adiposity. Until the present invention, such a pharmacological agent was unknown.

The present invention provides biologically active anti-obesity proteins. Such agents therefore allow patients to overcome their obesity handicap and live normal lives with a more normalized risk for type II diabetes, cardiovascular disease and cancer.

SUMMARY OF INVENTION

The present invention is directed to a biologically active anti-obesity protein of the Formula (I):

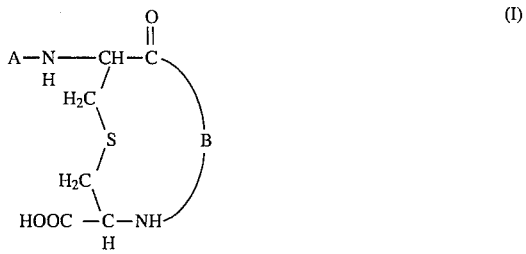

wherein:
A is SEQ ID NO: 1; and
B is SEQ ID NO: 2.

The invention further provides a method of treating obesity, which comprises administering to a mammal in need thereof a protein of the Formula (I).

The invention further provides a pharmaceutical formulation, which comprises a protein of the Formula (I) together with one or more pharmaceutical acceptable diluents, carriers or excipients therefor.

DETAILED DESCRIPTION

For purposes of the present invention, as disclosed and claimed herein, the following terms and abbreviations are defined as follows:

Base pair (bp)—refers to DNA or RNA. The abbreviations A,C,G, and T correspond to the 5'-monophosphate forms of the nucleotides (deoxy)adenine, (deoxy)cytidine, (deoxy)guanine, and (deoxy)thymine, respectively, when they occur in DNA molecules. The abbreviations U,C,G, and T correspond to the 5'-monophosphate forms of the nucleosides uracil, cytidine, guanine, and thymine, respectively when they occur in RNA molecules. In double stranded DNA, base pair may refer to a partnership of A with T or C with G. In a DNA/RNA heteroduplex, base pair may refer to a partnership of T with U or C with G.

DNA—Deoyxribonucleic acid.

mRNA—messenger RNA.

Plasmid—an extrachromosomal self-replicating genetic element.

Reading frame—the nucleotide sequence from which translation occurs "read" in triplets by the translational apparatus of tRNA, ribosomes and associated factors, each triplet corresponding to a particular amino acid. Because each triplet is distinct and of the same length, the coding sequence must be a multiple of three. A base pair insertion or deletion (termed a frameshift mutation) may result in two different proteins being coded for by the same DNA segment. To insure against this, the triplet codons corresponding to the desired polypeptide must be aligned in multiples of three from the initiation codon, i.e. the correct "reading frame" must be maintained.

Recombinant DNA Cloning Vector—any autonomously replicating agent including, but not limited to, plasmids and phages, comprising a DNA molecule to which one or more additional DNA segments can or have been added.

Recombinant DNA Expression Vector—any recombinant DNA cloning vector in which a promoter has been incorporated.

Replicon—A DNA sequence that controls and allows for autonomous replication of a plasmid or other vector.

RNA—ribonucleic acid.

RP-HPLC—an abbreviation for reversed-phase high performance liquid chromatography.

Transcription—the process whereby information contained in a nucleotide sequence of DNA is transferred to a complementary RNA sequence.

Translation—the process whereby the genetic information of messenger RNA is used to specify and direct the synthesis of a polypeptide chain.

Tris—an abbreviation for tris(hydroxymethyl)aminomethane.

Treating—describes the management and care of a patient for the purpose of combating the disease, condition, or disorder and includes the administration of a compound of present invention to prevent the onset of the symptoms or complications, alleviating the symptoms or complications, or eliminating the disease, condition, or disorder. Treating obesity therefor includes the inhibition of food intake, the inhibition of weight gain, and inducing weight loss in patients in need thereof.

Vector—a replicon used for the transformation of cells in gene manipulation bearing polynucleotide sequences corresponding to appropriate protein molecules which, when combined with appropriate control sequences, confer specific properties on the host cell to be transformed. Plasmids, viruses, and bacteriophage are suitable vectors, since they are replicons in their own right. Artificial vectors are constructed by cutting and joining DNA molecules from different sources using restriction enzymes and ligases. Vectors include Recombinant DNA cloning vectors and Recombinant DNA expression vectors.

X-gal—an abbreviation for 5-bromo-4-chloro-3-idolyl beta-D-galactoside.

SEQ ID NO: 1 refers to the sequence set forth in the sequence listing and means an amino acid sequence of the formula:

SEQ ID NO: 1

| 1 | | | | 5 | | | | | 10 | | | | | 15 |
|---|---|---|---|---|---|---|---|---|---|---|---|---|---|---|
| Val | Pro | Ile | Xaa | Lys | Val | Xaa | Asp | Asp | Thr | Lys | Thr | Leu | Ile | Lys |
| | | | | 20 | | | | | 25 | | | | | 30 |
| Thr | Ile | Val | Thr | Arg | Ile | Xaa | Asp | Ile | Ser | His | Xaa | Xaa | Ser | Val |
| | | | | 35 | | | | | 40 | | | | | 45 |
| Ser | Ser | Lys | Xaa | Lys | Val | Thr | Gly | Leu | Asp | Phe | Ile | Pro | Gly | Leu |
| | | | | 50 | | | | | 55 | | | | | 60 |
| His | Pro | Ile | Leu | Thr | Leu | Ser | Lys | Xaa | Asp | Xaa | Thr | Leu | Ala | Val |
| | | | | 65 | | | | | 70 | | | | | 75 |
| Tyr | Xaa | Xaa | Ile | Leu | Thr | Ser | Xaa | Pro | Ser | Arg | Xaa | Val | Ile | Xaa |
| | | | | 80 | | | | | 85 | | | | | 90 |
| Ile | Ser | Xaa | Asp | Leu | Glu | Xaa | Leu | Arg | Asp | Leu | Leu | His | Val | Leu |
| | | | | 95 | | | | | | | | | | |
| Ile | Phe | Ser | Lys | Ser | | | | | | | | | | | wherein:
Xaa at position 4 of SEQ ID NO: 1 is Gln or Glu;
Xaa at position 7 of SEQ ID NO: 1 is Gln or Glu;
Xaa at position 22 of SEQ ID NO: 1 is Gln, Asn, or Asp;
Xaa at position 27 of SEQ ID NO: 1 is Thr or Ala;
Xaa at position 28 of SEQ ID NO: 1 is Gln, Glu, or absent;
Xaa at position 34 of SEQ ID NO: 1 is Gln or Glu;
Xaa at position 54 of SEQ ID NO: 1 is Met, methionine sulfoxide, Leu, Ile, Val, Ala, or Gly;
Xaa at position 56 of SEQ ID NO: 1 is Gln or Glu;
Xaa at position 62 of SEQ ID NO: 1 is Gln or Glu;
Xaa at position 63 of SEQ ID NO: 1 is Gln or Glu;
Xaa at position 68 of SEQ ID NO: 1 is Met, methionine sulfoxide, Leu, Ile, Val, Ala, or Gly;
Xaa at position 72 of SEQ ID NO: 1 is Gln, Asn, or Asp;
Xaa at position 75 of SEQ ID NO: 1 is Gln or Glu;
Xaa at position 78 of SEQ ID NO: 1 is Gln, Asn, or Asp; and
Xaa at position 82 of SEQ ID NO: 1 is Gln, Asn, or Asp.

SEQ ID NO: 2 refers to the sequence set forth in the sequence listing and means an amino acid sequence of the formula:

SEQ ID NO: 2

| 1 | | | | 5 | | | | | 10 | | | | | 15 |
|---|---|---|---|---|---|---|---|---|---|---|---|---|---|---|
| His | Leu | Pro | Xaa | Ala | Ser | Gly | Leu | Glu | Thr | Leu | Xaa | Ser | Leu | Gly |
| | | | | 20 | | | | | 25 | | | | | 30 |
| Gly | Val | Leu | Glu | Ala | Ser | Gly | Tyr | Ser | Thr | Glu | Val | Val | Ala | Leu |

-continued
SEQ ID NO: 2

```
                          35                    40                      45
     Ser  Arg  Leu  Xaa  Gly  Ser  Leu  Xaa  Asp  Xaa  Leu  Xaa  Xaa  Leu  Asp
     Leu  Ser  Pro  Gly
``` wherein:
Xaa at position 4 of SEQ ID NO: 2 is Gln, Trp, Tyr, Phe, Ile, Val, or Leu;
Xaa at position 12 of SEQ ID NO: 2 is Asp or Glu;
Xaa at position 34 of SEQ ID NO: 2 is Gln or Glu;
Xaa at position 38 of SEQ ID NO: 2 is Gln or Glu;
Xaa at position 40 of SEQ ID NO: 2 is Met, methionine sulfoxide, Leu, Ile, Val, Ala, or Gly;
Xaa at position 42 of SEQ ID NO: 2 is Gln, Trp, Tyr, Phe, Ile, Val, or Leu; and
Xaa at position 43 of SEQ ID NO: 2 is Gln or Glu.

The amino acids abbreviations are accepted by the United States Patent and Trademark Office as set forth in 37 C.F.R. § 1.822 (b)(2) (1993). One skilled in the art would recognize that certain amino acids are prone to rearrangement. For example, Asp may rearrange to aspartimide and isoasparigine as described in I. Schön et al., *Int. J. Peptide Protein Res.* 14: 485–94 (1979) and references cited therein. These rearrangement derivatives are included within the scope of the present invention. Unless otherwise indicated the amino acids are in the L configuration.

As noted above the present invention provides a protein of the Formula (I):

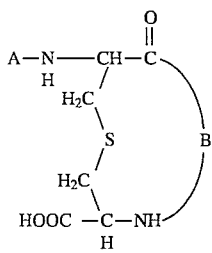

wherein:
A is SEQ ID NO: 1; and
B is SEQ ID NO: 2.

The preferred proteins of the present invention are those of Formula (i) wherein:
Xaa at position 4 of SEQ ID NO: 1 is Gln;
Xaa at position 7 of SEQ ID NO: 1 is Gln;
Xaa at position 22 of SEQ ID NO: 1 is Asn;
Xaa at position 27 of SEQ ID NO: 1 is Thr;
Xaa at position 28 of SEQ ID NO: 1 is Gln;
Xaa at position 34 of SEQ ID NO: 1 is Gln;
Xaa at position 54 of SEQ ID NO: 1 is Met;
Xaa at position 56 of SEQ ID NO: 1 is Gln;
Xaa at position 62 of SEQ ID NO: 1 is Gln;
Xaa at position 63 of SEQ ID NO: 1 is Gln;
Xaa at position 68 of SEQ ID NO: 1 is Met;
Xaa at position 72 of SEQ ID NO: 1 is Gln;
Xaa at position 75 of SEQ ID NO: 1 is Gln;
Xaa at position 78 of SEQ ID NO: 1 is Asn;
Xaa at position 82 of SEQ ID NO: 1 is Asn;
Xaa at position 4 of SEQ ID NO: 2 is Trp;
Xaa at position 12 of SEQ ID NO: 2 is Asp;
Xaa at position 34 of SEQ ID NO: 2 is Gln;
Xaa at position 38 of SEQ ID NO: 2 is Gln;
Xaa at position 40 of SEQ ID NO: 2 is Met;
Xaa at position 42 of SEQ ID NO: 2 is Trp; and
Xaa at position 43 of SEQ ID NO: 2 is Gln.

Yiying Zhang et al. in *Nature* 372: 425–32 (December 1994) report the cloning of the murine obese (ob) mouse gene and present mouse DNA and the naturally occurring amino acid sequence of the obesity protein for the mouse and human. This protein is speculated to be a hormone that is secreted by fat cells and controls body weight. The naturally occurring amino acid sequence of the obesity protein contains two cysteine residues; thus, providing a means to form a di-sulfide bond in the naturally occurring protein. The present invention is directed at replacing the single di-sulfide bond with a thioether bond. That is, cystine is chemically converted to lanthionine. The claimed lanthionine containing protein is more chemically stable. The protein is more bioavailable than the naturally occurring protein. Furthermore, the claimed peptide demonstrates greater serum stability and is therefore, longer acting. Thus, the present invention provides a biologically active protein, which is effective treatment for obesity.

The protein with unmodified cysteine residues is ordinarily prepared by recombinant DNA technology. Techniques for making substitutional mutations at predetermined sites in DNA having a known sequence are well known, for example M13 primer mutagenesis. The mutations that might be made in the DNA must not place the sequence out of reading frame and preferably will not create complementary regions that could produce secondary mRNA structure. See DeBoer et al., EP 75,444A (1983).

The compounds of the present invention may be prepared by substituting the cystine residue with lanthionine by dissolving the peptides in an aqueous solvent, preferably urea and adjusting the pH to about pH 11 to 12 with a base such as sodium hydroxide, potassium hydroxide or ammonium hydroxide at a temperature between about 4° C. to about 37° C. The temperature of the reaction is preferably 30° C. to 37° C. An acceptable protein concentration is from about 0.1 to 10 mg/mL. Preferably, the reaction is carried out at 1 mg/mL to 2 mg/mL. To aid in the formation of lanthionine and to improve the reaction yield, dithiothreitol (DTT) or other reducing agent may be added to the reaction mixture after adjusting the pH to about pH 11 to 12.

The claimed proteins may be purified from the reaction mixture by standard techniques appreciated in the art such as reversed phase chromatography, affinity chromatography, ion exchange chromatography, and size exclusion chromatography.

The protein with unmodified cysteine residues may be produced either by recombinant DNA technology or well known chemical procedures, such as solution or solid-phase peptide synthesis, or semi-synthesis in solution beginning with protein fragments coupled through conventional solution methods. The protein with unmodified cysteine residues may then be converted to the claimed protein by techniques taught herein. However, one skilled in the art would recognize that the claimed proteins can be produced directly by well known chemical procedures.

RECOMBINANT SYNTHESIS

The protein with unmodified cysteine residues may be produced by recombinant methods. Recombinant methods are preferred if a high yield is desired. The basic steps in the recombinant production of protein include:

a) construction of a synthetic or semi-synthetic (or isolation from natural sources) DNA encoding the protein with unmodified cysteine residues, b) integrating the coding sequence into an expression vector in a manner suitable for the expression of the protein either alone or as a fusion protein, c) transforming an appropriate eukaryotic or prokaryotic host cell with the expression vector, and d) recovering and purifying the recombinantly produced protein.

1.a. Gene Construction

Synthetic genes, the in vitro or in vivo transcription and translation of which will result in the production of the protein may be constructed by techniques well known in the art. Owing to the natural degeneracy of the genetic code, the skilled artisan will recognize that a sizable yet definite number of DNA sequences may be constructed which encode the protein with unmodified cysteine residues. In the preferred practice of the invention, synthesis is achieved by recombinant DNA technology.

Methodology of synthetic gene construction is well known in the art. For example, see Brown, et al. (1979) Methods in Enzymology, Academic Press, N.Y., Vol. 68, pgs. 109–151. The DNA sequence corresponding to the synthetic protein gene may be generated using conventional DNA synthesizing apparatus such as the Applied Biosystems Model 380A or 380B DNA synthesizers (commercially available from Applied Biosystems, Inc., 850 Lincoln Center Drive, Foster City, Calif. 94404).

It may be desirable in some applications to modify the coding sequence of the protein so as to incorporate a convenient protease sensitive cleavage site, e.g., between the signal peptide and the structural protein facilitating the controlled excision of the signal peptide from the fusion protein construct.

The gene encoding the protein with unmodified cysteine residues may also be created by using polymerase chain reaction (PCR). The template can be a cDNA library (commercially available from CLONETECH or STRATAGENE) or mRNA isolated from human adipose tissue. Such methodologies are well known in the art Maniatis, et al. *Molecular Cloning: A Laboratory Manual*, Cold Spring Harbor Press, Cold Spring Harbor Laboratory, Cold Spring Harbor, N.Y. (1989).

1.b. Direct Expression or Fusion Protein

The protein with unmodified cysteine residues may be made either by direct expression or as fusion protein comprising the protein followed by enzymatic or chemical cleavage. A variety of peptidases (e.g. trypsin) which cleave a polypeptide at specific sites or digest the peptides from the amino or carboxy termini (e.g. diaminopeptidase) of the peptide chain are known. Furthermore, particular chemicals (e.g. cyanogen bromide) will cleave a polypeptide chain at specific sites. The skilled artisan will appreciate the modifications necessary to the amino acid sequence (and synthetic or semi-synthetic coding sequence if recombinant means are employed) to incorporate site-specific internal cleavage sites. See e.g., Carter P., Site Specific Proteolysis of Fusion Proteins, Ch. 13 in *Protein Purification: From Molecular Mechanisms to Large Scale Processes*, American Chemical Soc., Washington, D.C. (1990).

1.c. Vector Construction

Construction of suitable vectors containing the desired coding and control sequences employ standard ligation techniques. Isolated plasmids or DNA fragments are cleaved, tailored, and religated in the form desired to form the plasmids required.

To effect the translation of the desired protein, one inserts the engineered synthetic DNA sequence into any of a plethora of appropriate recombinant DNA expression vectors through the use of appropriate restriction endonucleases. A synthetic coding sequence is designed to possess restriction endonuclease cleavage sites at either end of the transcript to facilitate isolation from and integration into these expression and amplification and expression plasmids. The isolated cDNA coding sequence may be readily modified by the use of synthetic linkers to facilitate the incorporation of this sequence into the desired cloning vectors by techniques well known in the art. The particular endonucleases employed will be dictated by the restriction endonuclease cleavage pattern of the parent expression vector to be employed. The choice of restriction sites are chosen so as to properly orient the coding sequence with control sequences to achieve proper in-frame reading and expression of the protein.

In general, plasmid vectors containing promoters and control sequences which are derived from species compatible with the host cell are used with these hosts. The vector ordinarily carries a replication site as well as marker sequences which are capable of providing phenotypic selection in transformed cells. For example, *E. coli* is typically transformed using pBR322, a plasmid derived from an *E. coli* species (Bolivar, et al., Gene 2: 95 (1977)). Plasmid pBR322 contains genes for ampicillin and tetracycline resistance and thus provides easy means for identifying transformed cells. The pBR322 plasmid, or other microbial plasmid must also contain or be modified to contain promoters and other control elements commonly used in recombinant DNA technology.

The desired coding sequence is inserted into an expression vector in the proper orientation to be transcribed from a promoter and ribosome binding site, both of which should be functional in the host cell in which the protein is to be expressed. An example of such an expression vector is a plasmid described in Belagaje et al., U.S. Pat. No. 5,304,493, the teachings of which are herein incorporated by reference. The gene encoding A-C-B proinsulin described in U.S. Pat. No. 5,304,493 can be removed from the plasmid pRB182 with restriction enzymes NdeI and BamHI. The genes encoding the protein with unmodified cysteine residues can be inserted into the plasmid backbone on a NdeI/BamHI restriction fragment cassette.

1.d. Procaryotic Expression

In general, procaryotes are used for cloning of DNA sequences in constructing the vectors useful in the invention. For example, *E. coli* K12 strain 294 (ATCC No. 31446) is particularly useful. Other microbial strains which may be used include *E. coli* B and *E. coli* X1776 (ATCC No. 31537). These examples are illustrative rather than limiting.

Prokaryotes also are used for expression. The aforementioned strains, as well as *E. coli* W3110 (prototrophic, ATCC No. 27325), bacilli such as *Bacillus subtilis,* and other enterobacteriaceae such as *Salmonella typhimurium* or *Serratia marcescans,* and various pseudomonas species may be used. Promoters suitable for use with prokaryotic hosts include the β-lactamase (vector pGX2907 [ATCC 39344] contains the replicon and β-lactamase gene) and lactose promoter systems (Chang et al., *Nature,* 275:615 (1978); and Goeddel et al., *Nature* 281:544 (1979)), alkaline phosphatase, the tryptophan (trp) promoter system (vector pATH1 [ATCC 37695] is designed to facilitate expression of an open reading frame as a trpE fusion protein under control of the trp promoter) and hybrid promoters such as the tac promoter (isolatable from plasmid pDR540 ATCC-37282). However, other functional bacterial promoters, whose nucleotide sequences are generally known, enable one of skill in the art to ligate them to DNA encoding the protein using linkers or adaptors to supply any required restriction sites. Promoters for use in bacterial systems also will contain a Shine-Dalgarno sequence operably linked to the DNA encoding protein.

1.e. Eucaryotic Expression

The protein with unmodified cysteine residues may be recombinantly produced in eukaryotic expression systems. Preferred promoters controlling transcription in mammalian host cells may be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. β-actin promoter. The early and late promoters of the SV40 virus are conveniently obtained as an SV40 restriction fragment which also contains the SV40 viral origin of replication. Fiers, et al., *Nature,* 273:113 (1978). The entire SV40 genome may be obtained from plasmid pBRSV, ATCC 45019. The immediate early promoter of the human cytomegalovirus may be obtained from plasmid pCMVβ (ATCC 77177). Of course, promoters from the host cell or related species also are useful herein.

Transcription of a DNA encoding the protein by higher eukaryotes is increased by inserting an enhancer sequence into the vector. Enhancers are cis-acting elements of DNA, usually about 10–300 bp, that act on a promoter to increase its transcription. Enhancers are relatively orientation and position independent having been found 5' (Laimins, L. et al., *PNAS* 78:993 (1981)) and 3' (Lusky, M. L., et al., *Mol. Cell Bio.* 3:1108 (1983)) to the transcription unit, within an intron (Banerji, J. L. et al., *Cell* 33:729 (1983)) as well as within the coding sequence itself (Osborne, T. F., et al., *Mol. Cell Bio.* 4:1293 (1984)). Many enhancer sequences are now known from mammalian genes (globin, RSV, SV40, EMC, elastase, albumin, alpha-fetoprotein and insulin). Typically, however, one will use an enhancer from a eukaryotic cell virus. Examples include the SV40 late enhancer, the cytomegalovirus early promoter enhancer, the polyoma enhancer on the late side of the replication origin, and adenovirus enhancers.

Expression vectors used in eukaryotic host cells (yeast, fungi, insect, plant, animal, human or nucleated cells from other multicellular organisms) will also contain sequences necessary for the termination of transcription which may affect mRNA expression. These regions are transcribed as polyadenylated segments in the untranslated portion of the mRNA encoding protein. The 3' untranslated regions also include transcription termination sites.

Expression vectors may contain a selection gene, also termed a selectable marker. Examples of suitable selectable markers for mammalian cells are dihydrofolate reductase (DHFR, which may be derived from the BglII/HindIII restriction fragment of pJOD-10 [ATCC 68815]), thymidine kinase (herpes simplex virus thymidine kinase is contained on the BamHI fragment of vP-5 clone [ATCC 2028]) or neomycin (G418) resistance genes (obtainable from pNN414 yeast artificial chromosome vector [ATCC 37682]). When such selectable markers are successfully transferred into a mammalian host cell, the transfected mammalian host cell can survive if placed under selective pressure. There are two widely used distinct categories of selective regimes. The first category is based on a cell's metabolism and the use of a mutant cell line which lacks the ability to grow without a supplemented media. Two examples are: CHO DHFR$^-$ cells (ATCC CRL-9096) and mouse LTK$^-$ cells (L-M(TK-) ATCC CCL-2.3). These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, Southern P. and Berg, P., *J. Molec. Appl. Genet.* 1: 327 (1982), mycophenolic acid, Mulligan, R. C. and Berg, P. *Science* 209:1422 (1980), or hygromycin, Sugden, B. et al., *Mol Cell. Biol.* 5:410–413 (1985). The three examples given above employ bacterial genes under eukaryotic control to convey resistance to the appropriate drug G418 or neomycin (geneticin), xgpt (mycophenolic acid) or hygromycin, respectively.

A preferred vector for eucaryotic expression is pRc/CMV. pRc/CMV is commercially available from Invitrogen Corporation, 3985 Sorrento Valley Blvd., San Diego, Calif. 92121. To confirm correct sequences in plasmids constructed, the ligation mixtures are used to transform *E. coli* K12 strain DH5a (ATCC 31446) and successful transformants selected by antibiotic resistance where appropriate. Plasmids from the transformants are prepared, analyzed by restriction and/or sequence by the method of Messing, et al., *Nucleic Acids Res.* 9:309 (1981).

Host cells may be transformed with the expression vectors of this invention and cultured in conventional nutrient media modified as is appropriate for inducing promoters, selecting transformants or amplifying genes. The culture conditions, such as temperature, pH and the like, are those previously used with the host cell selected for expression, and will be apparent to the ordinarily skilled artisan. The techniques of transforming cells with the aforementioned vectors are well known in the art and may be found in such general references as Maniatis, et al., *Molecular Cloning: A Laboratory Manual,* Cold Spring Harbor Press, Cold Spring Harbor Laboratory, Cold Spring Harbor, N.Y. (1989), or *Current Protocols in Molecular Biology* (1989) and supplements.

Preferred suitable host cells for expressing the vectors encoding the proteins in higher eukaryotes include: African green monkey kidney line cell line transformed by SV40 (COS-7, ATCC CRL-1651); transformed human primary embryonal kidney cell line 293, (Graham, F. L. et al., *J. Gen Virol.* 36:59–72 (1977), *Virology* 77:319–329, *Virology* 86:10–21); baby hamster kidney cells (BHK-21(C-13), ATCC CCL-10, *Virology* 16:147 (1962)); chinese hamster ovary cells CHO-DHFR⁻ (ATCC CRL-9096), mouse Sertoli cells (TM4, ATCC CRL-1715, *Biol. Reprod.* 23:243–250 (1980)); african green monkey kidney cells (VERO 76, ATCC CRL-1587); human cervical epitheloid carcinoma cells (HeLa, ATCC CCL-2); canine kidney cells (MDCK, ATCC CCL-34); buffalo rat liver cells (BRL 3A, ATCC CRL-1442); human diploid lung cells (WI-38, ATCC CCL-75); human hepatocellular carcinoma cells (Hep G2, ATCC HB-8065); and mouse mammary tumor cells (MMT 060562, ATCC CCL51).

1.f. Yeast Expression

In addition to prokaryotes, eukaryotic microbes such as yeast cultures may also be used. Saccharomyces cerevisiae, or common baker's yeast is the most commonly used eukaryotic microorganism, although a number of other strains are commonly available. For expression in Saccharomyces, the plasmid YRp7, for example, (ATCC-40053, Stinchcomb, et al., *Nature* 282:39 (1979); Kingsman et al., *Gene* 7:141 (1979); Tschemper et al., *Gene* 10:157 (1980)) is commonly used. This plasmid already contains the trp gene which provides a selection marker for a mutant strain of yeast lacking the ability to grow in tryptophan, for example ATCC no. 44076 or PEP4-1 (Jones, *Genetics* 85:12 (1977)).

Suitable promoting sequences for use with yeast hosts include the promoters for 3-phosphoglycerate kinase (found on plasmid pAP12BD ATCC 53231 and described in U.S. Pat. No. 4,935,350, Jun. 19, 1990) or other glycolytic enzymes such as enolase (found on plasmid pAC1 ATCC 39532), glyceraldehyde-3-phosphate dehydrogenase (derived from plasmid pHcGAPC1 ATCC 57090, 57091), zymomonas mobilis (U.S. Pat. No. 5,000,000 issued Mar. 19, 1991), hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein (contained on plasmid vector pCL28XhoLHBPV ATCC 39475, U.S. Pat. No. 4,840,896), glyceraldehyde 3-phosphate dehydrogenase, and enzymes responsible for maltose and galactose (GAL1 found on plasmid pRY121 ATCC 37658) utilization. Suitable vectors and promoters for use in yeast expression are further described in R. Hitzeman et al., European Patent Publication No. 73,657A. Yeast enhancers such as the UAS Gal from Saccharomyces cerevisiae (found in conjunction with the CYC1 promoter on plasmid YEpsec—hI1beta ATCC 67024), also are advantageously used with yeast promoters.

The protein with unmodified cysteine residue refers to the protein translated off the ribosome. One skilled in the art would recognize that the cysteine can be converted to inter or intra molecular cystine by in vitro oxidation, or by cellular mechanisms.

The following examples and preparations are presented to further illustrate the preparation of the claimed proteins. The scope of the present invention is not to be construed as merely consisting of the following examples.

PREPARATION 1

A DNA sequence encoding the following protein sequence:

SEQ ID NO: 3

| 1 | | | | 5 | | | | | 10 | | | | | 15 |
|---|---|---|---|---|---|---|---|---|---|---|---|---|---|---|
| Val | Pro | Ile | Gln | Lys | Val | Gln | Asp | Asp | Thr | Lys | Thr | Leu | Ile | Lys |
| | | | | 20 | | | | | 25 | | | | | 30 |
| Thr | Ile | Val | Thr | Arg | Ile | Asn | Asp | Ile | Ser | His | Thr | Gln | Ser | Val |
| | | | | 35 | | | | | 40 | | | | | 45 |
| Ser | Ser | Lys | Gln | Lys | Val | Thr | Gly | Leu | Asp | Phe | Ile | Pro | Gly | Leu |
| | | | | 50 | | | | | 55 | | | | | 60 |
| His | Pro | Ile | Leu | Thr | Leu | Ser | Lys | Met | Asp | Gln | Thr | Leu | Ala | Val |
| | | | | 65 | | | | | 70 | | | | | 75 |
| Tyr | Gln | Gln | Ile | Leu | Thr | Ser | Met | Pro | Ser | Arg | Asn | Val | Ile | Gln |
| | | | | 80 | | | | | 85 | | | | | 90 |
| Ile | Ser | Asn | Asp | Leu | Glu | Asn | Leu | Arg | Asp | Leu | Leu | His | Val | Leu |
| | | | | 95 | | | | | 100 | | | | | 105 |
| Ala | Phe | Ser | Lys | Ser | Cys | His | Leu | Pro | Trp | Ala | Ser | Gly | Leu | Glu |
| | | | | 110 | | | | | 115 | | | | | 120 |
| Thr | Leu | Asp | Ser | Leu | Gly | Gly | Val | Leu | Glu | Ala | Ser | Gly | Tyr | Ser |
| | | | | 125 | | | | | 130 | | | | | 135 |
| Thr | Glu | Val | Val | Ala | Leu | Ser | Arg | Leu | Gln | Gly | Ser | Leu | Gln | Asp |
| | | | | 140 | | | | | 145 | | | | | |
| Met | Leu | Trp | Gln | Leu | Asp | Leu | Ser | Pro | Gly | Cys | | | | | is obtained using standard PCR methodology. A forward primer (5'-GG GG CAT ATG AGG GTA CCT ATC CAG AAA GTC CAG GAT GAC AC) SEQ ID. No: 4 and a reverse primer (5'-GG GG GGATC CTA TTA GCA CCC GGG AGA CAG GTC CAG CTG CCA CAA CAT) SEQ ID No: 5 is used to amplify sequences from a human fat cell library (commercially available from CLONETECH). The PCR product is cloned into PCR-Script (available from STRATAGENE) and sequenced.

PREPARATION 2

Vector Construction

A plasmid containing the DNA sequence encoding the desired protein is constructed to include NdeI and BamHI restriction sites. The plasmid carrying the cloned PCR product is digested with NdeI and BamHI restriction enzymes. The small~450 bp fragment is gel-purified and ligated into the vector pRB182 from which the coding sequence for A-C-B proinsulin is deleted. The ligation products are transformed into *E. coli* DH10B (commercially available from GIBCO-BRL) and colonies growing on tryptone-yeast (DIFCO) plates supplemented with 10 μg/mL of tetracycline are analyzed. Plasmid DNA is isolated, digested with NdeI and BamHI and the resulting fragments are separated by agarose gel electrophoresis. Plasmids containing the expected~450 bp NdeI to BamHI fragment are kept. *E. coli* B BL21 (DE3) (commercially available from NOVOGEN) are transformed with this second plasmid expression suitable for culture for protein production.

The techniques of transforming cells with the aforementioned vectors are well known in the art and may be found in such general references as Maniatis, et al. (1988) *Molecular Cloning: A Laboratory Manual*, Cold Spring Harbor Press, Cold Spring Harbor Laboratory, Cold Spring Harbor, N.Y. or *Current Protocols in Molecular Biology* (1989) and supplements. The techniques involved in the transformation of *E. coli* cells used in the preferred practice of the invention as exemplified herein are well known in the art. The precise conditions under which the transformed *E. coli* cells are cultured is dependent on the nature of the *E. coli* host cell line and the expression or cloning vectors employed. For example, vectors which incorporate thermoinducible promoter-operator regions, such as the cI857 thermoinducible lambda-phage promoter-operator region, require a temperature shift from about 30 to about 40 degrees C. in the culture conditions so as to induce protein synthesis.

In the preferred embodiment of the invention *E. coli* K12 RV308 cells are employed as host cells but numerous other cell lines are available such as, but not limited to, *E. coli* K12 L201, L687, L693, L507, L640, L641, L695, L814 (*E. coli* B). The transformed host cells are then plated on appropriate media under the selective pressure of the antibiotic corresponding to the resistance gene present on the expression plasmid. The cultures are then incubated for a time and temperature appropriate to the host cell line employed.

Proteins which are expressed in high-level bacterial expression systems characteristically aggregate in granules or inclusion bodies which contain high levels of the overexpressed protein. Kreuger et al., in *Protein Folding*, Gierasch and King, eds., pgs 136–142 (1990), American Association for the Advancement of Science Publication No. 89-18S, Washington, D.C. Such protein aggregates must be solubilized to provide further purification and isolation of the desired protein product. Id.

Preferably, the present proteins are expressed as Met-Arg protein so that the expressed proteins may be readily converted to the protein with Cathepsin C. The purification of proteins is by techniques known in the art and includes reversed phase chromatography, affinity chromatography, ion exchange chromatography, and size exclusion.

The claimed proteins are prepared by dissolving the protein with unmodified cysteine residues in a urea solution (about 3 to about 8M, preferably 7M). The pH is raised to about pH 11 to about pH 12. The solution is allowed to incubate at the elevated pH at a temperature between about 4° C. to about 37° C. for between 4 and 72 hours. The protein may be treated with a reducing compound such as DTT. Two likely intermediates are of the Formula (II):

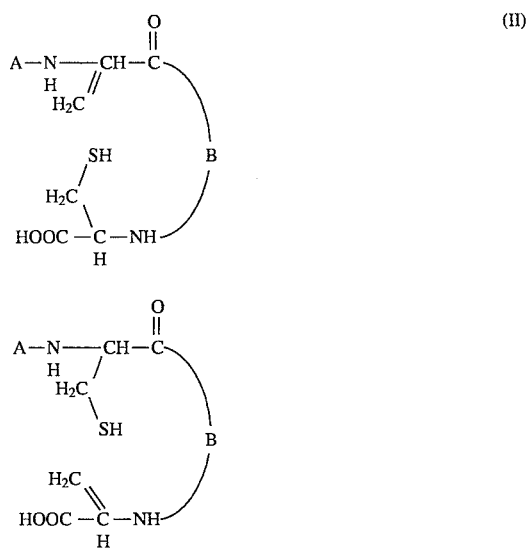

wherein:
 A is SEQ ID NO: 1; and
 B is SEQ ID NO: 2.

These intermediates are unstable and quickly convert to the more stable lanthionine compounds of the Formula (I). However, one skilled in the art would recognize that depending on the conditions used and the reducing agent employed other intermediates are possible. This reaction is further illustrated in the following Example.

EXAMPLE 1

The pH of 1 mg/mL solution of cystine containing peptide of SEQ ID No: 3 is adjusted to pH 12 with NaOH and held at 37° C. The reaction is monitored with an SDS gel assay to measure non-reducible peptide. At the completion of the reaction, the lanthionine containing peptide is purified by reversed phase chromatography with an acetonitrile gradient.

The compounds of Formula (I) may exist, particularly when formulated, as dimers, trimers, tetramers, and other multimers. Such multimers are included within the scope of the present invention.

The present invention provides a method for treating obesity. The method comprises administering to the organism an effective amount of anti-obesity protein in a dose between about 1 and 1000 μg/kg. A preferred dose is from about 10 to 100 μg/kg of active compound. A typical daily dose for an adult human is from about 0.5 to 100 mg. In practicing this method, compounds of the Formula (I) can be administered in a single daily dose or in multiple doses per day. The treatment regime may require administration over extended periods of time. The amount per administered dose or the total amount administered will be determined by the physician and depend on such factors as the nature and severity of the disease, the age and general health of the patient and the tolerance of the patient to the compound.

The invention further provides pharmaceutical formulations comprising compounds of the Formula (I). The proteins, preferably in the form of a pharmaceutically acceptable salt, can be formulated for parenteral administration for the therapeutic or prophylactic treatment of obesity. For example, compounds of the Formula (I) can be admixed with conventional pharmaceutical carriers and excipients. The compositions comprising claimed proteins contain from about 0.1 to 90% by weight of the active protein, preferably in a soluble form, and more generally from about 10 to 30%. Furthermore, the present proteins may be administered alone or in combination with other anti-obesity agents or agents useful in treating diabetes.

For intravenous (i.v.) use, the protein is administered in commonly used intravenous fluid(s) and administered by infusion. Such fluids, for example, physiological saline, Ringer's solution or 5% dextrose solution can be used.

For intramuscular preparations, a sterile formulation, preferably a suitable soluble salt form of a protein of the Formula (I), for example the hydrochloride salt, can be dissolved and administered in a pharmaceutical diluent such as pyrogen-free water (distilled), physiological saline or 5% glucose solution. A suitable insoluble form of the compound may be prepared and administered as a suspension in an aqueous base or a pharmaceutically acceptable oil base, e.g. an ester of a long chain fatty acid such as ethyl oleate.

The ability of the present compounds to treat obesity is demonstrated in vivo as follows:

BIOLOGICAL TESTING FOR ANTI-OBESITY PROTEINS

Parabiotic experiments suggest that a protein is released by peripheral adipose tissue and that the protein is able to control body weight gain in normal, as well as obese mice. Therefore, the most closely related biological test is to inject the test article by any of several routes of administration (e.g. i.v., s.c., i.p., or by minipump or cannula) and then to monitor food and water consumption, body weight gain, plasma chemistry or hormones (glucose, insulin, ACTH, corticosterone, GH, T4) over various time periods. Suitable test animals include normal mice (ICR, etc.) and obese mice (ob/ob, Avy/a, KK-Ay, tubby, fat). The ob/ob mouse model of obesity and diabetes is generally accepted in the art as being indicative of the obesity condition. Controls for non-specific effects for these injections are done using vehicle with or without the active agent of similar composition in the same animal monitoring the same parameters or the active agent itself in animals that are thought to lack the receptor (db/db mice, fa/fa or cp/cp rats). Proteins demonstrating activity in these models will demonstrate similar activity in other mammals, particularly humans.

Since the target tissue is expected to be the hypothalamus where food intake and lipogenic state are regulated, a similar model is to inject the test article directly into the brain (e.g. i.c.v. injection via lateral or third ventricles, or directly into specific hypothalamic nuclei (e.g. arcuate, paraventricular, perifornical nuclei). The same parameters as above could be measured, or the release of neurotransmitters that are known to regulate feeding or metabolism could be monitored (e.g. NPY, galanin, norepinephrine, dopamine, β-endorphin release).

Similar studies are accomplished in vitro using isolated hypothalamic tissue in a perifusion or tissue bath system. In this situation, the release of neurotransmitters or electrophysiological changes is monitored.

The compounds are active in at least one of the above biological tests and are anti-obesity agents. As such, they are useful in treating obesity and those disorders implicated by obesity. However, the proteins are not only useful as therapeutic agents; one skilled in the art recognizes that the proteins are useful in the production of antibodies for diagnostic use and, as proteins, are useful as feed additives for animals. Furthermore, the compounds are useful for controlling weight for cosmetic purposes in mammals. A cosmetic purpose seeks to control the weight of a mammal to improve bodily appearance. The mammal is not necessarily obese. Such cosmetic use forms part of the present invention.

---

We claim:

1. A compound of the Formula:

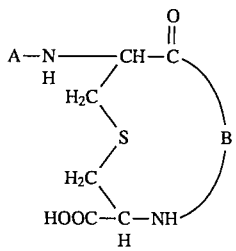

wherein:

A is SEQ ID NO: 1; and

B is SEQ ID NO: 2; or a pharmaceutically acceptable salt thereof.

2. A compound of claim 1, wherein

Xaa at position 4 of SEQ ID NO: 1 is Gln;

Xaa at position 7 of SEQ ID NO: 1 is Gln;

Xaa at position 22 of SEQ ID NO: 1 is Asn;

Xaa at position 27 of SEQ ID NO: 1 is Thr;

Xaa at position 28 of SEQ ID NO: 1 is Gln;

Xaa at position 34 of SEQ ID NO: 1 is Gln;

Xaa at position 54 of SEQ ID NO: 1 is Met;

Xaa at position 56 of SEQ ID NO: 1 is Gln;

Xaa at position 62 of SEQ ID NO: 1 is Gln;

Xaa at position 63 of SEQ ID NO: 1 is Gln;

Xaa at position 68 of SEQ ID NO: 1 is Met;

Xaa at position 72 of SEQ ID NO: 1 is Gln;

Xaa at position 75 of SEQ ID NO: 1 is Gln;

Xaa at position 78 of SEQ ID NO: 1 is Asn; and

Xaa at position 82 of SEQ ID NO: 1 is Asn.

3. A protein of claim 2, wherein

Xaa at position 4 of SEQ ID NO: 2 is Trp;

Xaa at position 12 of SEQ ID NO: 2 is Asp;

Xaa at position 34 of SEQ ID NO: 2 is Gln;

Xaa at position 38 of SEQ ID NO: 2 is Gln;

Xaa at position 40 of SEQ ID NO: 2 is Met;

Xaa at position 42 of SEQ ID NO: 2 is Trp; and

Xaa at position 43 of SEQ ID NO: 2 is Gln.

4. A pharmaceutical formulation, which comprises a protein of claim 1 together with one or more pharmaceutical acceptable diluents, carriers or excipients therefor.

5. A pharmaceutical formulation, which comprises a protein of claim 2 together with one or more pharmaceutical acceptable diluents, carriers or excipients therefor.

6. A pharmaceutical formulation, which comprises a protein of claim 3 together with one or more pharmaceutical acceptable diluents, carriers or excipients therefor.

* * * * *

UNITED STATES PATENT AND TRADEMARK OFFICE
CERTIFICATE OF CORRECTION

PATENT NO. : 5,594,101

DATED : January 14, 1997

INVENTOR(S) : Gerald W. Becker, et al.

It is certified that error appears in the above-identified patent and that said Letters Patent is hereby corrected as shown below:

Column 3, SEQ ID NO: 1, at position 91, reads "Ile"; should read --Ala--

Signed and Sealed this

Twenty-second Day of September, 1998

Attest:

BRUCE LEHMAN

*Attesting Officer*    *Commissioner of Patents and Trademarks*

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 95 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Modified-site
        ( B ) LOCATION: 4
        ( D ) OTHER INFORMATION: /note= "Xaa at position 4 of SEQ ID
          NO. 1 is Gln or Glu;"

( i x ) FEATURE:

(A) NAME/KEY: Modified-site
(B) LOCATION: 7
(D) OTHER INFORMATION: /note= "Xaa at position 7 of SEQ ID
NO. 1 is Gln or Glu;"

(ix) FEATURE:
(A) NAME/KEY: Modified-site
(B) LOCATION: 22
(D) OTHER INFORMATION: /note= "Xaa at position 22 of SEQ
ID NO. 1 is Gln, Asn or Asp;"

(ix) FEATURE:
(A) NAME/KEY: Modified-site
(B) LOCATION: 27
(D) OTHER INFORMATION: /note= "Xaa at position 27 of SEQ
ID NO. 1 is Thr or Ala;"

(ix) FEATURE:
(A) NAME/KEY: Modified-site
(B) LOCATION: 28
(D) OTHER INFORMATION: /note= "Xaa at position 28 of SEQ
ID NO. 1 is Gln, Glu or absent;"

(ix) FEATURE:
(A) NAME/KEY: Modified-site
(B) LOCATION: 34
(D) OTHER INFORMATION: /note= "Xaa at position 34 of SEQ
ID NO. is Gln or Glu;"

(ix) FEATURE:
(A) NAME/KEY: Modified-site
(B) LOCATION: 54
(D) OTHER INFORMATION: /note= "Xaa at position 54 of SEQ
ID NO. is Met, methionine sulfoxide, Leu, Ile, Val, Ala,
or Gly;"

(ix) FEATURE:
(A) NAME/KEY: Modified-site
(B) LOCATION: 56
(D) OTHER INFORMATION: /note= "Xaa at position 56 of SEQ
ID NO. 1 is Gln or Glu;"

(ix) FEATURE:
(A) NAME/KEY: Modified-site
(B) LOCATION: 62
(D) OTHER INFORMATION: /note= "Xaa at position 62 of SEQ
ID NO. 1 is Gln or Glu;"

(ix) FEATURE:
(A) NAME/KEY: Modified-site
(B) LOCATION: 63
(D) OTHER INFORMATION: /note= "Xaa at position 63 of SEQ
ID NO. 1 is Gln or Glu;"

(ix) FEATURE:
(A) NAME/KEY: Modified-site
(B) LOCATION: 68
(D) OTHER INFORMATION: /note= "Xaa at position 68 of SEQ
ID NO. 1 is Met, methionine sulfoxide, Leu, Ile, Val,
Ala or Gly;"

(ix) FEATURE:
(A) NAME/KEY: Modified-site
(B) LOCATION: 72
(D) OTHER INFORMATION: /note= "Xaa at position 72 of SEQ
ID NO. 1 is Gln, Asn, or Asp;"

(ix) FEATURE:
(A) NAME/KEY: Modified-site
(B) LOCATION: 75
(D) OTHER INFORMATION: /note= "Xaa at position 75 of SEQ
ID NO. 1 is Gln or Glu;"

(ix) FEATURE:
(A) NAME/KEY: Modified-site
(B) LOCATION: 78
(D) OTHER INFORMATION: /note= "Xaa at position 78 of SEQ
ID NO. 1 is Gln, Asn, or Asp;"

(ix) FEATURE:

(A) NAME/KEY: Modified-site
(B) LOCATION: 82
(D) OTHER INFORMATION: /note= "Xaa at position 82 of SEQ
    ID NO. 1 is Gln, Asn, or Asp."

(xi) SEQUENCE DESCRIPTION: SEQ ID NO:1:

| Val | Pro | Ile | Xaa | Lys | Val | Xaa | Asp | Asp | Thr | Lys | Thr | Leu | Ile | Lys | Thr |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Ile | Val | Thr | Arg | Ile | Xaa | Asp | Ile | Ser | His | Xaa | Xaa | Ser | Val | Ser | Ser |
|     |     |     | 20  |     |     |     |     | 25  |     |     |     |     | 30  |     |     |
| Lys | Xaa | Lys | Val | Thr | Gly | Leu | Asp | Phe | Ile | Pro | Gly | Leu | His | Pro | Ile |
|     |     | 35  |     |     |     |     | 40  |     |     |     |     | 45  |     |     |     |
| Leu | Thr | Leu | Ser | Lys | Xaa | Asp | Xaa | Thr | Leu | Ala | Val | Tyr | Xaa | Xaa | Ile |
|     | 50  |     |     |     |     | 55  |     |     |     |     | 60  |     |     |     |     |
| Leu | Thr | Ser | Xaa | Pro | Ser | Arg | Xaa | Val | Ile | Xaa | Ile | Ser | Xaa | Asp | Leu |
| 65  |     |     |     |     | 70  |     |     |     |     | 75  |     |     |     |     | 80  |
| Glu | Xaa | Leu | Arg | Asp | Leu | Leu | His | Val | Leu | Ala | Phe | Ser | Lys | Ser |     |
|     |     |     |     | 85  |     |     |     |     | 90  |     |     |     |     | 95  |     |

(2) INFORMATION FOR SEQ ID NO:2:

(i) SEQUENCE CHARACTERISTICS:
    (A) LENGTH: 49 amino acids
    (B) TYPE: amino acid
    (C) STRANDEDNESS: single
    (D) TOPOLOGY: linear (ii) MOLECULE TYPE: protein (ix) FEATURE:
    (A) NAME/KEY: Modified-site
    (B) LOCATION: 4
    (D) OTHER INFORMATION: /note= "Xaa at poisition 4 of SEQ
        ID NO. 2 is Gln, Trp, Tyr, Phe, Ile, Val, or Leu;"

(ix) FEATURE:
    (A) NAME/KEY: Modified-site
    (B) LOCATION: 12
    (D) OTHER INFORMATION: /note= "Xaa at position 12 of SEQ
        ID NO. 2 is Asp or Glu;"

(ix) FEATURE:
    (A) NAME/KEY: Modified-site
    (B) LOCATION: 34
    (D) OTHER INFORMATION: /note= "Xaa at position 34 of SEQ
        ID NO. 2 is Gln or Glu;"

(ix) FEATURE:
    (A) NAME/KEY: Modified-site
    (B) LOCATION: 38
    (D) OTHER INFORMATION: /note= "Xaa at position 38 of SEQ
        ID NO. 2 is Gln or Glu;"

(ix) FEATURE:
    (A) NAME/KEY: Modified-site
    (B) LOCATION: 40
    (D) OTHER INFORMATION: /note= "Xaa at position 40 of SEQ
        ID NO. 2 is Met, methionine sulfoxide, Leu, Ile, Val,
        Ala, or Gly;"

(ix) FEATURE:
    (A) NAME/KEY: Modified-site
    (B) LOCATION: 42
    (D) OTHER INFORMATION: /note= "Xaa at position 42 of SEQ
        ID NO. 2 is Gln, Trp, Tyr, Phe, Ile, Val, or Leu; "

(ix) FEATURE:
    (A) NAME/KEY: Modified-site
    (B) LOCATION: 43
    (D) OTHER INFORMATION: /note= "Xaa at position 43 of SEQ
        ID NO. 2 is Gln or Glu;"

(xi) SEQUENCE DESCRIPTION: SEQ ID NO:2:

```
      His Leu Pro Xaa Ala Ser Gly Leu Glu Thr Leu Xaa Ser Leu Gly Gly
      1               5                   10                  15

Val Leu Glu Ala Ser Gly Tyr Ser Thr Glu Val Val Ala Leu Ser Arg
                      20              25                  30

Leu Xaa Gly Ser Leu Xaa Asp Xaa Leu Xaa Xaa Leu Asp Leu Ser Pro
              35              40                      45

Gly
```

( 2 ) INFORMATION FOR SEQ ID NO:3:

( i ) SEQUENCE CHARACTERISTICS:
        ( A ) LENGTH: 146 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:3:

```
      Val Pro Ile Gln Lys Val Gln Asp Asp Thr Lys Thr Leu Ile Lys Thr
      1               5                   10                  15

Ile Val Thr Arg Ile Asn Asp Ile Ser His Thr Gln Ser Val Ser Ser
                      20              25                  30

Lys Gln Lys Val Thr Gly Leu Asp Phe Ile Pro Gly Leu His Pro Ile
                  35              40                  45

Leu Thr Leu Ser Lys Met Asp Gln Thr Leu Ala Val Tyr Gln Gln Ile
          50              55                  60

Leu Thr Ser Met Pro Ser Arg Asn Val Ile Gln Ile Ser Asn Asp Leu
      65                  70                  75                  80

Glu Asn Leu Arg Asp Leu Leu His Val Leu Ala Phe Ser Lys Ser Cys
                      85                  90                  95

His Leu Pro Trp Ala Ser Gly Leu Glu Thr Leu Asp Ser Leu Gly Gly
                  100             105                 110

Val Leu Glu Ala Ser Gly Tyr Ser Thr Glu Val Val Ala Leu Ser Arg
                  115             120                 125

Leu Gln Gly Ser Leu Gln Asp Met Leu Trp Gln Leu Asp Leu Ser Pro
          130             135                 140

Gly Cys
      145
```

( 2 ) INFORMATION FOR SEQ ID NO:4:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: protein ( x i ) SEQUENCE DESCRIPTION: SEQ ID NO:4:

```
GGGGCATATG AGGGTACCTA TCCAGAAAGT CCAGGATGAC AC                          42
```

( 2 ) INFORMATION FOR SEQ ID NO:5:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: protein ( x i ) SEQUENCE DESCRIPTION: SEQ ID NO:5:

GGGGGGATCC  TATTAGCACC  CGGGAGACAG  GTCCAGCTGC  CACAACAT          4 8